(12) United States Patent
Raoult et al.

(10) Patent No.: US 7,410,787 B1
(45) Date of Patent: Aug. 12, 2008

(54) DIAGNOSIS OF WHIPPLE'S DISEASE

(75) Inventors: Didier Raoult, Marseilles (FR);
Bernard La Scola, Rousset (FR);
Marie-Laure Birg, Marseilles (FR);
Florence Fenollar, Marseilles (FR)

(73) Assignee: Protisvalor Mediterranee, Marseilles (FR)

( * ) Notice: Subject to any disclaimer, the term of this patent is extended or adjusted under 35 U.S.C. 154(b) by 0 days.

(21) Appl. No.: 09/936,921

(22) PCT Filed: Mar. 24, 2000

(86) PCT No.: PCT/FR00/00754

§ 371 (c)(1),
(2), (4) Date: Sep. 24, 2001

(87) PCT Pub. No.: WO00/58440

PCT Pub. Date: Oct. 5, 2000

(30) Foreign Application Priority Data

Mar. 26, 1999 (FR) .................................. 99 03989
May 21, 1999 (FR) .................................. 99 06679

(51) Int. Cl.
*C12N 1/20* (2006.01)
*C12N 1/00* (2006.01)
*C12N 5/02* (2006.01)
*A61K 39/00* (2006.01)
*G01N 33/53* (2006.01)

(52) U.S. Cl. ..................... 435/252.1; 435/7.32; 435/41; 435/243; 435/325; 435/383; 435/392; 424/93.1; 424/178.1

(58) Field of Classification Search ................ 435/69.1, 435/69.7, 7.32, 325, 41, 243, 252.1, 383, 435/392; 424/93.1, 178.1, 184.1; 514/44
See application file for complete search history.

(56) References Cited

U.S. PATENT DOCUMENTS 5,047,330 A 9/1991 Grassi et al.
6,083,683 A * 7/2000 Pace et al. .................... 435/4

OTHER PUBLICATIONS

Drancourt 1999 Presse Medicale, vol. 2: No. 8, Feb. 27, 1999, pp. 435-439 (translated).*
Harlow and Lane 1986, Cold Spring Harbor Laboratory 1988, (chapter 14).*
Relman 1997(J.I.D. 176: 752-754).*
Kent ( abstract only, ARCH.PATHOL.LAB.MED 1980, 104 (10) 544-547.*
Relman et al., "Identification of the Uncultured Bacillus of Whipple's Disease", The New England Journal of Medicine, vol. 327, Jul. 30, 1992, No. 5, pp. 293-301.
Drancourt, "*Tropheryma whippelii*, pathogene emergent a culture intracellulaire responsible de la maladie de Whipple", Presse Medicale, vol. 28, No. 8, Feb. 27, 1999, pp. 435-439.
Mollet et al., "rpoB sequence analysis as a novel basis for bacterial identification", Molecular Microbiology, vol. 26, No. 5, 1997, pp. 1005-1011.
Von Herbay et al., "Diagnostic Application of a Polymerase Chain Reaction Assay for the Whipple's Disease Bacterium to Intestinal Biopsies", vol. 110, 1996, pp. 1735-1743.
Schoedon, G. et al., "Deactivation of macrophages with interleukin-4 is the key to the isolation of *Tropheryma whippelii*," Journal of Infectious Diseases, vol. 176, No. 3, pp. 672-677, 1997.
Zaaijer, H. L. et al., "De ziekte van Whipple," Nederlands Tijdschrift Voor Geneeskunde, vol. 143, No. 8, pp. 388-392, 1999.
Muller, C. et al., "Cultivation of *T. whippelii* from peripheral blood mononuclear cells," GASTROENTEROLOGY, vol. 116, No. 4, Part 2, p. A910, 1999.
Raoult, D. et al., "Cultivation of the bacillus of Whipple's disease," The New England Journal of Medicine, vol. 342, No. 9, pp. 620-625, 2000.
Kim, B. J. et al., "Identification of mycobacterial species by comparative sequence analysis of the RNA polymerase gene (rpoB)," Journal of Clinical Microbiology, vol. 37, No. 6, pp. 1714-1720, 1999.
Hinrikson, H. P., "Detection of three different types of '*Tropheryma whippelii*' directly from clinical specimens by sequencing single-strand conformation polymorphism (SSCP) analysis and type specific PCR of their 16S-23S ribosomal intergenic spacer region," International Journal of Systematic Bacteriology, vol. 49, pp. 1701-1706, 1999.

* cited by examiner

*Primary Examiner*—Shanon A. Foley
*Assistant Examiner*—Padma V Baskar
(74) *Attorney, Agent, or Firm*—Oliff & Berridge, PLC (57) ABSTRACT

The invention relates to a method for in vitro seriological diagnosis of Whipple's disease, whereby the bacteria responsible for the disease are isolated and established in a culture and brought into contact with the serum or biological fluid of an infected patient. The invention also relates to useful oligonucelotides with a probe and a primer for amplifying, sequencing and detecting the gene rpoB of the bacteria, *Tropheryma whippelii*.

42 Claims, 4 Drawing Sheets

DIAGNOSIS OF WHIPPLE'S DISEASE

The present invention relates to the field of diagnostics. More precisely, the invention relates to a method for the in vitro serological diagnosis of Whipple's disease and to a device for carrying out this method. The invention further relates to a kit for in vitro detection of the bacterium responsible for Whipple's disease.

The present invention further relates to the field of the techniques of detection and/or amplification and sequencing with the aid of oligonucleotide probes or primers and to their application to tests for detecting the presence of bacteria of the species *Tropheryma whippelii* or to their identification.

BACKGROUND OF THE INVENTION

Whipple's disease is a disease which manifests itself in a variety of forms. The most classic form is that of a fever with chronic diarrhea leading to weight loss, but this disease is also capable of giving rise to chronic articular symptoms, cerebral symptoms with dementia and also cardiac symptoms, particularly endocarditis with negative hemoculture.

Since it was first described in 1907, Whipple's disease has been understood to involve the existence of a bacterium associated with "intestinal lipodystrophy" due to the observation of numerous microorganisms after the silver staining of a mesenteric ganglion (Whipple, Bull. John Hopkins Hosp. 1907; 18: 328–391). Demonstration of the non-specific PAS-positive (PAS=periodic acid-Schiff) character of this bacterium and subsequent observations by electron microscopy confirm the presence of an intracellular bacterial species of Gram-positive structure (Chears et al., Gastroenterology 1961; 41: 129–138). The universal molecular tool 16S rRNA made it possible to confirm this hypothesis, specifying the phylogenic taxonomy of this novel bacterial species and assigning to it the provisional name *Tropheryma whippelii* to evoke the idea of intestinal malabsorption and to honor the discoverer of the complaint (Relman et al., N. Engl. J. Med. 1992; 327: 293–301). The direct sequencing of 721 bases of an amplified fragment from a biopsy of one patient's small intestine (Wilson et al., Lancet 1991; 338: 474–475) and then from another patient's ganglion (Wilson et al., ASM News 1992; 58: 318–321) confirms the novelty of the bacterial species associated with Whipple's disease. The sequencing by Relman et al. (op. cit.) of 1321 bases in one sample, representing 90% of the gene, and of a fragment of 284 bases in four other patients made it possible to confirm that the bacterial species associated with Whipple's disease represented a novel species, and to specify its taxonomic position in the phylum of the actinomycetes, i.e. the bacteria of Gram-positive structure with a high content of guanosine plus cytosine, representing a new branch relatively close to two species known in human pathology, namely *Actinomyces pyogenes* and *Rothia dentocariosa*.

The disease is currently diagnosed by microscopic observation, after staining, of a smear obtained from a biopsy, or by amplification and sequencing of the universal genetic tool 16S rRNA (Relman et al., op. cit.).

Hitherto, it has in fact been impossible to isolate and cultivate the bacterium responsible for Whipple's disease in a manner suitable for performing serological tests.

Contrary to all expectation, the Applicant has developed a method of culturing the bacterium responsible for Whipple's disease.

SUMMARY OF THE INVENTION

The inventors have discovered that the cell culture which enables the bacterium *Tropheryma whippelii* to be isolated and multiplied must have both a long lifetime and a slow multiplication time. They have in fact demonstrated that the doubling time of the bacterium is very long (18 days). Preferably, the primary culture should even be carried out directly on immortalized cells.

Earlier studies carried out on primary cultures of human blood monocytes (SHOEDON et al., "Journal of Infectious Diseases", volume 176, number 3, 1997, pages 672–677) could not be used as a basis for establishing the bacterium *Tropheryma whippelii* in culture in such a way that it multiplied, because the mean lifetime of these monocytes is only 30 days, which is insufficient in view of the doubling time of the bacterium.

In addition, if the cells multiply too rapidly relative to the growth time of the bacterium, they cannot be cultivated because a dilution effect takes place and it becomes impossible to segregate the infected cells from the non-infected cells.

In one advantageous embodiment, the inventors used immortalized fibroblasts. These fibroblasts spread out over the bottom of the culture dish, cease multiplying when they have filled the whole of the cellular mat, but can be kept alive for several months under these conditions.

More precisely, the method of bacterial isolation and culture described in detail in Examples 1 and 2 below comprises inoculating human fibroblasts of the HEL line with a ground heart valve preparation in MEM. The bacterium responsible for Whipple's disease was isolated and established in culture after incubation for a minimum of two months, the culture medium being replaced regularly. The expression "established in culture" is understood as meaning that the bacterium is obtained reproducibly and multiplies over time, especially via successive subcultures on a cell culture.

The present invention therefore relates to the bacterium isolated and established in this way as an antigen source. This bacterium has been deposited in the Collection Nationale de Cultures de Microorganismes (CNCM) (Institut Pasteur, 28, rue du Dr Roux, 75724, Paris Cedex 15, France) under Deposit No. I-2202 and under the identification reference TWIST-Marseille. The deposit was made on May 19, 1999, under the terms of the Budapest Treaty.

The present invention further relates to an antigen of the bacterium according to the invention. More particularly, the present invention relates to an antigen which is a protein selected from those with molecular weights of about 10, 20, 35, 50, 60, 80, 100, 120, 150, 170 and 200 kD determined by polyacrylamide gel electrophoresis using the SDS-PAGE technique and by Western blotting.

The present invention further relates to a specific antibody directed against the bacterium or an antigen according to the invention, more particularly a polyclonal antibody of animal origin, especially a mouse or rabbit immunoglobulin, or a monoclonal antibody, especially a monoclonal antibody produced by the hybridoma deposited in the Collection Nationale de Cultures de Microorganismes (CNCM) (Institut Pasteur, 28, rue du Dr Roux, 75724, Paris Cedex 15, France) under the Deposit No. I-2411 and under the identification reference TW 17G2. The deposit was made on Mar. 22, 2000, under the terms of the Budapest Treaty.

The present invention further relates to the detection of an antibody specific for a human immunoglobulin which recognizes said bacterium, preferably IgG, IgM or IgA, and more particularly an animal immunoglobulin, especially an anti-human goat immunoglobulin.

The present invention further relates more particularly to an antigen, characterized in that it is a protein of 200 kD which reacts with a monoclonal antibody produced by the above-mentioned hybridomas according to the invention.

The present invention further relates to the use of a bacterium, an antigen of the bacterium or a specific antibody according to the invention in a method for the in vitro diagnosis of diseases associated with infections caused by the bacterium *Tropheryma whippelii*, and to a method for serological diagnosis of the infection caused by the bacterium *Tropheryma whippelii* according to the invention, which comprises bringing the serum or any other biological fluid of a patient into contact with said bacterium and detecting an immunological reaction.

DETAILED DESCRIPTION OF THE INVENTION

More particularly, the present invention relates to a method for the in vitro serological diagnosis of infections caused by *Tropheryma whippelii*, wherein the bacterium according to the invention, an antigen of the bacterium according to the invention or a specific antibody according to the invention is brought into contact with a sample taken from the patient and consisting of a human serum, biological fluid or swab.

The method according to the invention comprises the step which consists essentially in detecting an immunological reaction between an antibody specific for the bacterium according to the invention and an antigen of said bacterium, or between an antibody specific for an immunoglobulin according to the invention which recognizes said bacterium and a said human immunoglobulin which recognizes said bacterium.

The present invention further relates to a method for the in vitro serological diagnosis of Whipple's disease, which comprises bringing the serum or any other biological fluid of a patient into contact with the bacterium as defined above, and detecting the immunological reaction.

In one embodiment, the diagnostic method according to the invention comprises:

depositing a solution of bacterium according to the invention, especially 0.5 to 5 µl and preferably 1 µl of said solution containing said bacterium, in or on a solid support;

introducing the test serum or biological fluid, preferably diluted, into or onto said support;

introducing a solution of a labeled antibody, especially an anti-human animal immunoglobulin specific for the human immunoglobulin, especially of the IgG, IgM or IgA type, which recognizes said bacterium, into or onto the support;

observing an incubation period;

rinsing the solid support if appropriate; and actually detecting the immunological reaction especially between a human antibody which recognizes said bacterium and said anti-human immunoglobulin.

Advantageously, the diagnostic method of the invention involves an enzyme immunoassay of the ELISA type or an immunofluorescent assay. More particularly, the method according to the invention comprises:

depositing a solution of bacterium, isolated and established as indicated above, in or on a solid support;

introducing the diluted test serum or biological fluid into or onto said support;

introducing a solution of labeled anti-human immunoglobulin into or onto the support;

observing an incubation period;

rinsing the solid support if appropriate; and actually detecting the immunological reaction.

The solid support used can be any device suitable for handling cellular and bacterial suspensions, especially tubes, glass slides, bijoux tubes or rigid microtiter plates made of polyethylene, polystyrene, polyvinyl chloride or nitrocellulose and containing microwells; glass slides are preferred.

The antibody detected is an immunoglobulin, especially of the G, M or A type, which is specific for the bacterium responsible for Whipple's disease. The type of labeling used for the anti-human immunoglobulin is enzymatic, radioactive or fluorescent labeling, this last type of labeling being preferred.

The expression "fluorescent labeling" means that the antibody has been rendered fluorescent with an appropriate fluorescent agent, such as fluorescein iso(thio)cyanate, combined with an animal immunoglobutin which recognizes the human antibody.

The expression "radioactive labeling" means that the antibody carries, either on an element of its structure, for example the constituent tyrosine residues, or on an appropriate radical which has been fixed thereto, a radioactive isotope which enables it to be assayed by counting the radioactivity associated therewith.

The expression "enzymatic labeling" means that the antibody is coupled with an enzyme which, when associated with appropriate reagents, allows a quantitative measurement of this specific antibody.

The substrate and reagents are chosen so that the final product of the reaction or reaction sequence caused by the enzyme and involving these substances is:

either a colored or fluorescent substance which diffuses into the liquid medium surrounding the test sample and which is subjected either to the final spectrophotometric or, respectively, fluorimetric measurement or to a visual evaluation, optionally against a color scale, or an insoluble colored substance which deposits on the test sample and which can be subjected either to measurement with a reflection photometer or to a visual evaluation, optionally against a color scale.

When using an antibody which has been rendered fluorescent, the fluorescence associated with the test sample is read off directly on an appropriate apparatus.

When using a radioactive probe, for example iodine 125, the radioactivity associated with the test sample is counted in a gamma counter by any appropriate mode of implementation and e.g. after solubilization of the cells with an alkaline solution (for example sodium hydroxide solution) and recovery of the solution containing the radioactivity by using an absorbent plug.

When using an enzyme on the specific antibody, the appearance of a colored or fluorescent product is obtained by adding a solution containing the enzyme substrate and one or more auxiliary reagents making it possible finally to obtain, as the reaction product, either a colored product soluble in the medium, or an insoluble colored product, or a soluble fluorescent product, as explained above. The light signal originating from the samples treated in this way is then measured with an apparatus appropriate to each case, namely a transmission or reflection photometer or a fluorimeter, respectively. Alternatively, the coloration obtained can also be evaluated visually, optionally with the help of a scale of colored solutions.

If alkaline phosphatase is used as the enzyme, this enzyme is coupled with the specific antibody by the method proposed by Boehringer Mannheim-Biochemica. The preferred substrates for this enzyme are paranitrophenyl phosphate if the final measurement is to be spectrophotometric, or 4-methylumbelliferyl phosphate is the measurement is to be fluorimetric, or 5-bromo-4-chloro-3-indolyl phosphate if an insoluble colored reaction product is to be obtained. β-Galactosidase can likewise be used as the enzyme, the preferred substrates being orthonitrophenyl β-D-galactopyranoside or 4-methylumbelliferyl β-D-galactopyranoside.

Preferably, the specific antibodies can be coupled with peroxidase. In this case the coupling process is based on that described by M. B. WILSON and P. K. NAKANE in Immunofluorescence and Related Staining Techniques, W. Knapp, K. Kolubar, G. Wicks ed., Elsevier/North Holland, Amsterdam 1978, pp. 215–224.

The reagents used to reveal the peroxidase conjugated with the specific antibodies contain hydrogen peroxide (enzyme substrate) and an appropriate chromogen, for example orthophenylenediamine or 2,2'-azinobis(3-ethylthiazoline-6-sulfonic) acid [ABTS], to give a colored final reaction product soluble in the medium, or 3,3'-diaminobenzidine, 3-amino-9-ethylcarbazole or 4-chloro-α-naphthol to give an insoluble final reaction product, or parahydroxyphenylpropionic acid to give a fluorescent reaction product soluble in the medium.

Another embodiment of the invention is the use of specific antibodies coupled with acetylcholinesterase.

Acetylcholinesterase is preferably coupled with the antibody by means of a process based on that described in French patent no. 2 550 799 or by a process which briefly comprises preparing fragments of the antibody by a known technique, modifying the enzyme by reaction with an appropriate heterobifunctional agent and, finally, coupling the resulting products. Other known processes for the construction of immunoenzymatic conjugates can also be used in this case.

The enzymatic activity specifically bound to the antigen recognized by the acetylcholinesterase conjugate is preferably revealed by the well-known technique which employs acetylthiocholine as the enzyme substrate and Ellman's reagent (5,5'-dithio-2-nitrobenzoic acid) as the chromogen using any variant suitable for the case in question, for example the one described by Pradelles et al. in Anal. Chem. 1985, 57: 1170–1173.

The chromogens mentioned are used as such or in the form of water-soluble salts.

The method of serological diagnosis of the invention is suitable for use in biology and/or anatomicopathological laboratories. For this purpose, the device proposed for carrying out this method comprises a solid support on or in which a solution containing the bacterium as defined above has been deposited.

According to another feature, the invention further relates to a kit for in vitro detection of the bacterium responsible for Whipple's disease. This kit comprises the following components:

a solution containing the bacterium or an antigen according to the invention; and/or a solution containing at least one antibody according to the invention; and/or a solution containing at least one antibody specific for a human immunoglobulin which recognizes said . . .

More particularly, the kit comprises:

a solution containing the bacterium responsible for Whipple's disease, isolated and established as described above, as a positive control;

a solution containing a labeled specific antibody; and optionally a washing solution.

The specific antibody used in the kit of the invention is advantageously labeled with a radioactive probe, an enzyme or a fluorescent agent.

When the specific antibody is labeled with an enzyme, the kit also comprises the enzyme substrate and one or more reagents for visualizing the enzymatic activity.

When the specific antibody is labeled with a fluorescent agent, it is preferred to use fluorescein iso(thio)cyanate.

In one preferred embodiment of the invention, the specific antibody used is an immunoglobulin, particularly a mouse immunoglobulin.

The present invention further relates to the rpoB gene of the bacterium *Tropheryma whippelii* according to the present invention. The sequence of the rpoB gene was determined by enzymatic amplification and direct automatic sequencing with consensus primers among a large number of other bacteria of different genera and species.

The rpoB gene codes for one of the subunits of bacterial RNA polymerase and constitutes a genetic marker enabling specific detection of the bacterium of the species *Tropheryma whippelii*.

More particularly, the present invention relates to a fragment of the rpoB gene, characterized in that it has the nucleotide sequence SEQ ID No 3 in the attached sequence listing.

The present invention therefore further relates to nucleic acid sequences specific for the species *Tropheryma whippelii* whose nucleotide sequence is derived from the rpoB gene of said bacterium and especially from the fragment of the rpoB gene referred to above.

According to Lazcano et al. [J. Mol. Evol. (1988) 27: 365–376], RNA polymerases are divided into two groups according to their origin, one consisting of RNA- or DNA-dependent viral RNA polymerases and the other consisting of DNA-dependent RNA polymerases of eukaryotic or prokaryotic origin (archaebacteria and eubacteria). Eubacterial DNA-dependent RNA polymerases are characterized by a simple and conserved multimeric constitution called a "core enzyme", represented by $\alpha\beta\beta'$, or a "holoenzyme", represented by $\alpha\beta\beta'\sigma$ [Yura and Ishihama, Ann. Rev. Genet. (1979) 13: 59–97].

Numerous studies have demonstrated the functional role, within the multimeric enzymatic complex, of the β subunit of eubacterial RNA polymerase. As far as archaebacterial and eukaryotic RNA polymerases are concerned, they have a more complex structure capable of reaching about ten or even about thirty subunits (Pühler et al., Proc. Natl. Acad. Sci. USA (1989) 86: 4569–4573].

The genes which code for the different $\alpha\beta\beta'\sigma$ subunits of DNA-dependent RNA polymerase in eubacteria, namely the rpoA, rpoB, rpoC and rpoD genes respectively, are classed in different groups comprising genes coding for constituent proteins of the ribosomal subunits or for enzymes involved in the replication and repair of the genome [Yura and Ishihama, Ann. Rev. Genet. (1979) 13: 59–97]. Some authors have shown that the nucleic acid sequences of the rpoB and rpoC genes can be used to construct phylogenic trees [Rowland et al., Biochem. Soc. Trans. (1992) 21: 40s], making it possible to separate the different branches and sub-branches among the kingdoms of the living.

Before this feature of the invention is explained in greater detail, various terms used in the description and the claims are defined below:

"nucleic acid extracted from bacteria" is understood as meaning either the whole nucleic acid, or the genomic DNA, or the messenger RNAs, or the DNA obtained from reverse transcription of the messenger RNAs.

"nucleotide fragment" and "oligonucleotide" are two synonymous terms denoting a concatenation of nucleotide units which is characterized by an information sequence of natural (or possibly modified) nucleic acids capable of hybridizing, like natural nucleic acids, with a complementary or substantially complementary nucleotide fragment under predetermined conditions of strict stringency. The concatenation can contain nucleotide units whose structure differs from that of natural nucleic acids. A nucleotide fragment (or oligonucleotide) can contain e.g. up to 100 nucleotide units. It contains generally at least 10 and particularly at least 12 nucleotide units and can be obtained from a natural nucleic acid molecule and/or by genetic recombination and/or by chemical synthesis.

a nucleotide unit is derived from a monomer which can be a natural nucleic acid nucleotide whose constituent elements are a sugar, a phosphate group and a nitrogen base selected from adenine, guanine, uracil, cytosine and thymine; alternatively, the monomer is a nucleotide modified in at least one of the three constituent elements listed above; by way of example, the modification can take place either at the bases, with modified bases such as inosine, 5-methyldeoxycytidine, deoxyuridine, 5-dimethylaminodeoxyuridine or any other modified base capable of hybridization, or at the sugar, for example by replacement of at least one deoxyribose with a polyamide [P. E. Nielsen et al., Science (1991) 254: 1497–1500], or at the phosphate group, for example by replacement with esters selected especially from diphosphates, alkyl- and arylphosphonates and phosphorothioates.

"information sequence" is understood as meaning any ordered series of nucleotide-type units whose chemical nature and whose order in a reference direction constitute information analogous to that given by the sequence of natural nucleic acids.

"hybridization" is understood as meaning the process during which, under appropriate conditions, two nucleotide fragments having sufficiently complementary sequences are capable of associating with one another via stable and specific hydrogen bonds to form a double strand. The hybridization conditions are determined by the "stringency", i.e. the rigor of the operating conditions. The greater the stringency, the more specific is the hybridization. The stringency is a function especially of the base composition of a probe/target duplex and by the degree of mismatch between two nucleic acids. The stringency can also be a function of the parameters of the hybridization reaction, such as the concentration and type of ionic species present in the hybridization solution, the nature and concentration of denaturing agents and/or the hybridization temperature. The stringency of the conditions under which a hybridization reaction has to be performed depends especially on the probes used. All these facts are well known and the appropriate conditions can optionally be determined in each case by means of routine experiments. In general, depending on the length of the probes used, the temperature of the hybridization reaction is between about 20 and 65° C., particularly between 35 and 65° C., in a saline solution with a concentration of about 0.8 to 1 M.

a "probe" is a nucleotide fragment comprising e.g. from 10 to 100 nucleotide units, especially from 12 to 35 nucleotide units, and possessing a hybridization specificity under given conditions for forming a hybridization complex with a nucleic acid which, in the present case, has a nucleotide sequence included either in a messenger RNA or in a DNA obtained by reverse transcription of said messenger RNA, i.e. a transcription product; a probe can be used for diagnostic purposes (especially capture or detection probes) or for therapeutic purposes.

a "capture probe" is immobilized or immobilizable on a solid support by any appropriate means, for example by covalent bonding, by adsorption or by direct synthesis on a solid. Examples of supports include microtiter plates and DNA chips.

a "detection probe" can be labeled with a marker selected e.g. from radioactive isotopes, enzymes, particularly those capable of acting on a chromogenic, fluorigenic or luminescent substrate (especially a peroxidase or an alkaline phosphatase), chromophoric chemicals, chromogenic, fluorigenic or luminescent compounds, nucleotide base analogs, and ligands such as biotin.

a "species probe" is a probe for identifying the species of a bacterium.

a "genus probe" is a probe for identifying the genus of a bacterium.

a "primer" is a probe comprising e.g. from 10 to 100 nucleotide units and possessing a hybridization specificity under given conditions for initiating an enzymatic polymerization, for example in an amplification technique such as PCR, in a sequencing process, in a transcription method, etc.

One subject of the present invention is a single-stranded oligonucleotide selected from oligonucleotides having a sequence of at least 12 consecutive nucleotide units included in one of the sequences SEQ ID No 4 and SEQ ID No 5 in the attached sequence listing, and from the oligonucleotides complementary to these oligonucleotides. These oligonucleotides can be oligodeoxyribonucleotides (DNAs) and oligoribonucleotides (RNAs) in which the "T" is replaced with "U".

In particular, an oligonucleotide according to the present invention possesses at least 12 units as described above and at most 50 units. More particularly, an oligonucleotide according to the present invention possesses from 12 to 35 units.

A preferred oligonucleotide has a sequence selected from the sequences SEQ ID No 4 and 5.

Inosine is capable of pairing with any other base.

The sequences SEQ ID No 4 and 5 can be prepared by chemical synthesis using the techniques well known to those skilled in the art and described e.g. in the article by Itakura K. et al. [(1984) Annu. Rev. Biochem. 53: 323].

A first application of an oligonucleotide of the invention is its use as a probe for detecting bacteria of the species *Tropheryma whippelii* in a biological sample, said probe comprising a nucleotide sequence of at least 12 consecutive nucleotide units included in one of the sequences SEQ ID No 4 and SEQ ID No 5 and their complementary sequences. In the remainder of the description, such a probe of the invention will be called a species probe.

The probes according to the invention can be used for diagnostic purposes in tests for detecting the presence or absence of a target nucleic acid in a sample by any of the known hybridization techniques, especially the techniques called "DOT-BLOT" [Maniatis et al. (1982) Molecular Cloning, Cold Spring Harbor], the DNA transfer techniques called "SOUTHERN BLOTTING" [Southern E. M., J. Mol. Biol. (1975) 98: 503], the RNA transfer techniques called "NORTHERN BLOTTING" or the so-called "sandwich" techniques [Dunn A. R., Hassel J. A. (1977) Cell 12: 23]. In particular, the "sandwich" technique is used with a capture probe and/or a detection probe, said probes being capable of hybridizing with two different regions of the target nucleic acid, and at least one of said probes (generally the detection probe) being capable of hybridizing with a region of the target which is specific for the species, it being understood that the capture probe and the detection probe must have at least partially different nucleotide sequences.

The nucleic acid to be detected (target) can be DNA or RNA (one or other optionally being obtained after amplification by PCR). In the case of the detection of a target of the double-stranded nucleic acid type, it is appropriate to denature the latter before carrying out the detection process. The target nucleic acid can be obtained by extraction from the nucleic acids of a test sample using the known methods. A double-stranded nucleic acid can be denatured by the known methods of chemical, physical or enzymatic denaturing and particularly by heating to an appropriate temperature above 80° C.

To carry out the above-mentioned hybridization techniques and particularly the "sandwich" techniques, one probe of the invention, called a capture probe, is immobilized on a solid support and another probe of the invention, called a detection probe, is labeled with a marker.

Examples of supports and markers are as defined above.

A further subject of the invention is a process for determining the presence or absence of a *Tropheryma whippelii* bacterium in a sample which contains or may contain nucleic acids of at least one such bacterium, said process comprising the steps which consist in bringing said sample into contact with at least one species probe of the invention and then determining, in a manner known per se, the formation or absence of formation of a hybridization complex between said probe and the nucleic acid of the sample.

Examples of how to detect the formation or absence of formation of a hybridization complex between said probe and the nucleic acid include the techniques described above, namely the "DOT-BLOT", "SOUTHERN BLOTTING" and "sandwich" techniques.

In one particular mode of carrying out this process for determining the presence or absence of the species *Tropheryma whippelii*, several species probes of the invention are used, it being understood that said probes are capable of hybridizing with non-overlapping regions of a nucleic acid corresponding to the rpoB gene of *Tropheryma whippelii*.

Advantageously, one species probe is immobilized on a solid support and another species probe is labeled with a marker.

Another application of an oligonucleotide of the invention is its use as a nucleotide primer comprising a single-stranded oligonucleotide selected from oligonucleotides having a sequence of at least 12 nucleotide units included in one of the sequences SEQ ID No 4 and 5, which primer can be used in the synthesis of a nucleic acid in the presence of a polymerase by a process known per se, especially in amplification methods using such a synthesis in the presence of a polymerase (PCR, RT-PCR, etc.). In particular, a primer of the invention can be used for the specific reverse transcription of a messenger RNA sequence of *Tropheryma whippelii* to give a corresponding complementary DNA sequence. Such a reverse transcription can constitute the first stage of the RT-PCR technique, the next stage being the amplification of the resulting complementary DNA by PCR. The primers of the invention can also be used for specific amplification of the total sequence of the DNA of the rpoB gene of *Tropheryma whippelii* by the polymerase chain reaction.

In one particular case, said primer comprising an oligonucleotide of the invention also comprises the sense or antisense sequence of a promoter recognized by an RNA polymerase (e.g. T7, T3 or SP6 promoter [Studier F. W., B. A. Moffatt (1986) J. Mol. Biol. 189: 113]: such primers can be used in nucleic acid amplification processes involving a transcription step, for example the NASBA or 3SR techniques [Van Gemen B. et al., Abstract MA 1091, 7th International Conference on A/DS (1991) Florence, Italy].

A further subject of the invention is a nucleotide primer comprising a single-stranded oligonucleotide selected from oligonucleotides having a sequence of at least 12 consecutive nucleotide units included in one of the sequences SEQ ID No 4 and SEQ ID No 5, which primer can be used for the total or partial sequencing of the rpoB gene of any strain of *Tropheryma whippelii*. In particular, the nucleotide primer can be used for the sequencing of an amplified nucleic acid, said sequencing giving the total or partial sequence of the rpoB gene by a process known per se, i.e. absorptive polymerization using dideoxynucleotides [Sanger F., Coulson A. R. (1975) J. Mol. Biol. 94: 441] or multiple hybridizations using DNA chips.

Preferably, in a use as a primer or for the sequencing of the rpoB genes, the sequences SEQ ID No 4 and 5 are used.

Finally, a last subject of the invention is a gene therapy probe for treating infections caused by a strain of *Tropheryma whippelii*, said probe comprising an oligonucleotide as defined above. This gene therapy probe, which is capable of hybridizing with the messenger RNA and/or the genomic DNA of said bacteria, can block the phenomena of translation and/or transcription and/or replication.

The principle of gene therapy methods is known and is based in particular on the use of a probe corresponding to an antisense strand: the formation of a hybrid between the probe and the sense strand is capable of perturbing at least one of the steps involving decryption of the genetic information. Gene therapy probes can therefore be used as antibacterial drugs for combating infections caused by spirochetes.

The invention will be understood more clearly with the aid of the following account divided into Examples. Said Examples relate to experiments performed for the purpose of putting the invention into effect and are given purely by way of illustration.

BRIEF DESCRIPTION OF THE DRAWINGS

FIG. 1 shows the SDS-PAGE protein profile of *Tropheryma whippelii*.

FIG. 2 shows the antigen profile of *Tropheryma whippelii* obtained by Western blotting, wherein the lanes contain the following:

Lane 1=immunized mouse serum,

Lane 2=immunized rabbit serum,

Lane 3=patient serum (IgG+IgM),

Lane 4=monoclonal antibody 1,

Lane 5=monoclonal antibody 2,

Lane 6=monoclonal antibody 3 and

Lane 7=monoclonal antibody 4.

FIG. 3 shows a Western blot performed on the strain TWIST no. I-2202 with the serum of a patient suffering from Whipple's disease, with IgM detection.

FIG. 4 shows the visualization of the product resulting from the amplification of the rpoB gene of *Tropheryma whippelii* with primers SEQ ID NOS:1 and 2 after staining with ethidium bromide, wherein the lanes contain the following:

Lane 1: *Tropherma whippelii*,

Lane 2: *Nocardia otitidiscaviarum*,

Lane 3: *Mycobaterium tuberculosis*,

Lane 4: *Staphylococcus epidermidis*,

Lane 5: *Corynebacterium amycolatum*,

Lane 6: *Mycobacterium avium*,

Lane 7: *Escherichia coli*,

Lane 8: $H_2O$ and

Lane 9: $H_2O$.

EXAMPLES

Example 1

Primary Isolation of the Bacterium

The primary isolation was effected by the centrifugation technique on bijoux tubes inoculated with human fibroblasts of the HEL line available from the ATCC. The HEL cells are cultivated on MEM (Gibco) supplemented with 10% of fetal calf serum (Gibco) and with 2 mM L-glutamine (Gibco). The bijoux tubes (Sterilin—Feltham—England, 3.7 ml), containing a carrier slide 12 mm in diameter, are inoculated with 1 ml of culture medium containing about 50,000 cells and incubated at 37° C. for 3 days under 5% of $CO_2$ to give a mat of confluent cells. The heart valve studied was ground in MEM and the suspension was used to inoculate the 3 bijoux tubes. These tubes were then centrifuged at 700 g for 1 hour at 22° C. The supernatant was then withdrawn and the mats were washed twice with sterile PBS and then incubated with 1 ml of medium at 37° C. under 5% of $CO_2$. The cultures were monitored by the cytocentrifugation of 100 μl of the supernatant in the bijoux tubes and Gimenez staining. This procedure was repeated after 10, 20 and 30 days. After 30 days the supernatant and the cellular mat in the bijoux tubes were harvested and subcultured on a confluent cellular mat in a 25 $cm^2$ culture dish (dish I) containing 15 ml of culture medium and incubated at 37° C. under 5% of $CO_2$. Every week for the next 6 weeks (D72), the cellular mat was examined under an inverted microscope to look for a cytopathogenic effect and the culture medium was replaced with fresh medium. Before the change of medium, 200 μl of supernatant were used to carry out a cytocentrifugation and Gimenez staining.

No cytopathogenic effect was detected before day 65. On day 72, small, dark and irregular inclusions could be detected in the HEL cells on examination of the cellular mat by inverted microscopy. After cytocentrifugation of the supernatant in dish I and Gimenez staining, several fine bacilli were detected, the majority of them being located inside the cells, where they appear smaller than the extracellular bacilli. Nevertheless, the majority were poorly stained, if at all, by Gimenez staining and appeared pale blue. Numerous bacilli were also detected after Gram staining. The majority appeared Gram-positive, but several were only partially violet or appeared Gram-negative. These bacilli are not acid-fast after Ziehl staining. After staining with PAS, the PAS-positive bacilli appeared more numerous than after the previous stainings. The majority of the long fine bacilli are observable outside the cells. The HEL cells appear filled with PAS-positive conglomerates and short fine PAS-positive bacilli.

Example 2

Propagation of the Isolate

The entire propagation procedure was carried out on HEL cells cultivated on MEM medium supplemented with 10% of fetal calf serum and with 2 mM L-glutamine, and incubated at 37° C. under 5% of $CO_2$. On day 75, 3 ml of supernatant in dish I were used to inoculate 10 bijoux tubes by the method described above and 2 ml of supernatant were used to inoculate a confluent cellular mat in a 25 $cm^2$ culture dish (dish A) containing 15 ml of medium. The cells in dish I and the remainder of the supernatant were harvested to give 10 ml of suspension. This suspension was then divided into five 2 ml aliquots. One of the aliquots was frozen in liquid nitrogen. Another aliquot was inoculated onto a confluent cellular mat in a 25 $cm^2$ culture dish (dish B) containing 15 ml of medium. The cells of another aliquot were lyzed by means of 4 freeze-thaw cycles using liquid nitrogen and warm water (55° C.) and then inoculated onto a confluent cellular mat in a 25 $cm^2$ culture dish (dish C) containing 15 ml of medium. Another aliquot was inoculated into a 25 $cm^2$ culture dish (dish D) containing 15 ml of medium but no cellular mat. On day 85 the medium in all these dishes and bijoux tubes was replaced with fresh medium. The cells were harvested and inoculated into a 75 $cm^2$ culture dish (dish D2) containing 30 ml of medium. Before the change of medium, 200 μl of supernatant were used to carry out a cytocentrifugation and staining with PAS and the remainder of the supernatant was frozen to be used as an antigen for serology. On days 95 and 105 the medium in all the dishes and bijoux tubes was changed as described above. Small portions of cellular mat were scraped in order to prepare cellular smears for staining with PAS. The efficiency of propagation of the strain was evaluated semi-quantitatively. The presence of PAS-positive bacilli was evaluated microscopically as follows with a magnification of 1000×: 0, absent; +, present but difficult to find; ++, easy to find but not present in all fields; +++, present in all fields. These evaluations were performed blind.

All the propagation methods proved efficient since they all enabled the isolate to be found after 30 days of subculture (Table 1). The semiquantitative evaluation made it possible to observe that the most efficient procedures are subculture in a bijoux tube, the subculture of supernatant (dish A) and the subculture of cells (dishes D, D2).

TABLE 1

|  |  | Bijoux tube | Dish A | Dish B | Dish C | Dish D | Dish D2 |
|---|---|---|---|---|---|---|---|
| Day 10 | Supernatant | + | − | + | − | + | NP |
| Day 20 | Supernatant | + | − | + | + | NP | − |
|  | Cellular smear | NP | + | + | + | NP | − |
| Day 30 | Supernatant | +++ | +++ | ++ | + | NP | ++ |
|  | Cellular smear | NP | ++ | + | + | NP | ++ |

NP: not performed

Example 3

Detection by Immunofluorescence

Intracellular bacteria were detected directly in a bijoux tube by immunofluorescence on day 105. After fixing with acetone, the tube was rinsed twice with PBS. 100 μl of the patient's serum, diluted to 1:50 with PBS containing 3% of skimmed milk powder, were added and the tube was incubated in a humid chamber at 37° C. for 30 min. After 3 rinses with PBS, the tube was incubated for 30 min at 37° C. with 100 μl of anti-human goat immunoglobulin labeled with fluorescein isothiocyanate (Fluoline H, BioMérieux, Marcy l'Etoile, France), diluted to 1:200 with PBS supplemented with 0.2% of Evans blue. After 3 rinses with PBS, the slide was mounted (cells facing downwards) in buffered glycerol (pH 8) and examined with a magnification of 400× using a Zeiss fluorescence microscope and a confocal microscope (LEICA DMIRBE) equipped with a 100× (NA. 1.4) immersion objective.

Examination by immunofluorescence shows that the staining with PAS and the other stainings underevaluate the cellular infection. On the slide, all the cells are filled with the bacterial antigen after 30 days of subculture. The study by confocal microscopy confirms the intracellular location of the bacterium. Several bacteria are detected in isolation in the form of fine bacilli resembling those observed after PAS staining. Nevertheless, most of the immunopositive material corresponds to larger inclusions where it is impossible to individualize bacteria. No immunopositive material is detected in the nucleus of the cells.

Example 4

Electron Microscopy

On day 105, 300 µl of a solution containing the cells harvested from dish D2 were prepared for study by electron microscopy. The cells were fixed in a 2.5% solution of glutaraldehyde in 0.1 M cacodylate buffer containing 0.1 M sucrose, for 1 h at 4° C. The cells were rinsed overnight in the same buffer and then fixed in osmium tetroxide in 0.1 M cacodylate buffer for 1 h at room temperature. Dehydration was effected by successive rinses in ethanol solutions of increasing concentration. The cells were then included in blocks of Epon 812. Thin sections were then cut from the blocks with an LKB Ultratome III microtome and subsequently stained with a saturated solution of uranyl acetate in methanol and an aqueous solution of lead citrate before being examined under a Jeol JEM 1200 EX electron microscope.

The electron microscope study confirms that the PAS-positive inclusions and the immunopositive material correspond to intact bacteria or bacteria undergoing degradation. The cytoplasmic membrane of these bacteria is composed of two layers dense to electrons. The thin bacterial wall is covered in places with an external pseudo-membrane, which gives a trilamellar appearance. Bacteria in the process of division are observed.

Example 5

Production of Mouse Polyclonal Antibodies Against the Bacterium Responsible for Whipple's Disease A mouse of the Balb C strain was injected intraperitoneally with 0.5 ml of supernatant containing $10^4$ bacteria responsible for Whipple's disease. The mouse was then reinjected 1, 2 and 3 weeks later with 0.5 ml of the same suspension. The mouse was bled 1 week after this last inoculation. The serum was tested on the one hand against a culture of the bacterium responsible for Whipple's disease and on the other hand against the valve of a patient suffering from Whipple's disease, once by immunofluorescence and once by the immunoperoxidase method. The revealing antibodies were anti-mouse antibodies labeled with fluorescein or with immunoperoxidase (supplied by Immunotech).

The bacteria could be visualized inside the cells. The present patent application therefore further relates to direct detection of the bacterium responsible for Whipple's disease in biopsies and various swabs, for example a heart valve, a digestive biopsy or a biopsy of any other organ suspected of being infected with the bacterium responsible for Whipple's disease.

Example 6

Production and Use of Monoclonal Antibodies to Products Against *Tropheryma whippelii*, Twist-Marseille Strain, and Determination of Antigens Equipment and Methods Strain of *Tropheryma whippelii*. The strain of *Tropheryma whippelii* used to produce and screen the hybridomas and test the specificity of the monoclonal antibodies (Mabs) is the TWIST-Marseille strain deposited in the CNCM under no. I-2202. *Tropheryma whippelii* was cultivated on embryonic human fibroblasts (HEL) under the culture conditions described above. On day 75 the infected cells from one flask were withdrawn . . . centrifuged for 10 minutes at 4000 g. The centrifugation residue was then resuspended in 5 ml of PBS. 0.5 ml of this suspension was inoculated into each mouse. The bacteria were also purified under a Renografin gradient and resuspended in deionized water for SDS-PAGE or in PBS for microimmunofluorescence (MIF).

Production of monoclonal antibodies (Mabs). Six-week-old female BALB/C mice were inoculated three times at 7-day intervals by the intraperitoneal injection of 0.5 ml of a suspension of *Tropheryma whippelii* TWIST-Marseille no. I-2202 in PBS. One week after the last of the 3 injections, the mice received an i.v. booster dose of 0.1 ml of a suspension of *Tropheryma whippelii* in PBS. Three days later, the spleen of the immunized mice was removed and the splenocytes were fused with SP2/0-Ag14 myeloma cells (10:1) using 50% polyethylene glycol (molecular weight: 1300–1600; Sigma Chemical Co., St Louis, Mo.). The fused cells were cultivated in a hybridoma culture medium (Seromed, Berlin, Germany) supplemented with 20% of fetal calf serum (Gibco BRL) and with hypoxanthine aminopterin-thymidine (Sigma Chemical Co., St Louis, Mo.), at 37° C. in a humid atmosphere enriched with 5% of $CO_2$.

The presence of anti-*T. whippelii* antibodies in the supernatant was detected by MIF. The positive hybridomas were subcultivated for the production of ascites. The isotypes of the Mabs were determined with the aid of the Immuno Type Mouse Monoclonal Antibody Isotyping Kit (SIGMA) containing IgM, IgA, IgG1, IgG2a, IgG2b and IgG3 mouse antisera (Sigma). The specificity of the Mabs was tested by Western blotting. One week after intraperitoneal injection of the mice with 0.5 ml of pristane (2,6,10,14-tetramethylpentadecane; Sigma), the ascites antibodies were produced by the intraperitoneal injection of a suspension of $3 \times 10^6$ hybridomas in 0.5 ml of PBS.

Microimmunofluorescence (MIF). MIF was used to screen the hybridomas and to determine the specificity of the Mabs. The antigens, consisting of cultures of *Tropheryma whippelii*, were deposited on 24-well slides using a quill. After fixing with methanol for 10 minutes at room temperature, the Mabs were deposited and incubated in a humid chamber at 37° C. for 30 minutes. The slides were subsequently rinsed for 2×5 minutes in PBS and then in distilled water, dried in air and then incubated for 30 minutes at 37° C. with anti-mouse IgM and anti-mouse IgG goat antibodies conjugated with fluorescein, diluted to 1/200 in PBS containing 0.2% of Evans blue (BioMérieux, Marcy l'Etoile, France). After rinsing, the slides were mounted using Fluorep (BioMérieux) and then read at a magnification of 400× under a fluorescence microscope (Axioskop 20; Carl Zeiss, Göttingen, Germany). The sera of the immunized mice were used as a positive control and the sera of the healthy mice as a negative control.

To detect the anti-*Tropheryma whippelii* antibodies in the serum of patients suffering from Whipple's disease, MIF was performed on Labtech slides [Raoult D. et al., N. Engl. J. Med., 2000]. The sera were diluted to 1:50, 1:100, 1:200, 1:400 and 1:800.

SDS-PAGE and Western blotting. SDS-PAGE and Western blotting were performed by Laemmli's method modified by the use of a 12% polyacrylamide separating gel and a 5% transfer gel. A suspension of *Tropheryma whippelii* containing 4 mg/ml of protein in buffer (0.0625 M Tris hydrochloride [pH 8.0], 2% of SDS, 5% of 2-mercaptoethanol, 10% of glycerol, 0.02% of bromophenol blue) was heated at 100° C. for 5 minutes. The dissolved antigens were separated by gel electrophoresis with a constant intensity of 8 to 10 mA for 3 to 4 hours in an electrophoresis cell (Mini Protein II: Bio Rad, Richmond, Calif.)(migration buffer: 25 mM Tris, 192 mM glycine, 0.1% of SDS). The size of the proteins was determined by comparison with a peptide weight marker (Low Range; Bio Rad). The antigens separated in this way were transferred to a nitrocellulose membrane (0.45 μm pores) using a transfer buffer (2.5 mM Tris, 192 mM glycine, 20% of methanol) under a current of 50 V for 1 hour at +4° C. in a Western blotting cell (Mini Trans-Blot; Bio Rad). After transfer, the nitrocellulose membranes were incubated overnight with 5% skimmed milk solution to block the non-specific binding sites. The membranes were subsequently washed 3 times in PBS and then dried in air. They were then incubated with the hybridoma supernatant diluted to 1:4 or with the patients' serum diluted to 1:100 in PBS supplemented with 3% of milk, at room temperature for 1 hour, and were then washed as described above. The membranes were subsequently incubated at room temperature for 1 hour with an F(ab')2 fragment of anti-mouse IgG goat antibody conjugated with peroxidase (Heavy and light chains: AffiniPure; Jackson ImmunoResearch), diluted to 1:500 in PBS supplemented with 3% of skimmed milk, and were then washed in PBS. The presence of specific antibodies was revealed by the presence of peroxidase activity using the substrate 4-chloro-1-naphthol.

Blind tests on the Mabs. The specificity of the monoclonal antibodies was evaluated blind by MIF on 19 bacteria: 12 species of *Bartonella*, namely 5 *B. quintana*, *B. henselae* Marseille, *B. henselae* Houston, *B. vinsonii* Baker, *B. elizabethae*, *B. grahamii*, *B. doshiae* and *B. taylorii*, *Coxiella burnetii* Nine Mile and a variety of 6 strains isolated in our laboratory from clinical samples, namely *Listeria monocytogenes*, *Staphylococcus aureus*, *Streptococcus bovis*, *Mycobacterium avium*, *Corynebacterium* ANF group and *Actinomyces mayerii*. After suspension in PBS and deposition on slides containing wells, the reactivity of the Mabs with the bacteria was estimated by MIF as described above with ascitic fluid diluted to 1:100.

Patients. 15 patients were tested: 8 patients with Whipple's disease located solely in the digestive system, which had been diagnosed by histology and/or the amplification of *T. whippelii* by PCR in digestive biopsies; and 7 patients suffering from endocarditis caused by *T. whippelii* . . . by PCR in valve biopsies.

Mice and rabbits. 5 mice and 1 rabbit were inoculated with a suspension of *T. whippelii* in order to determine what antigens would be recognized by the antibody response.

Results

Figure 1:
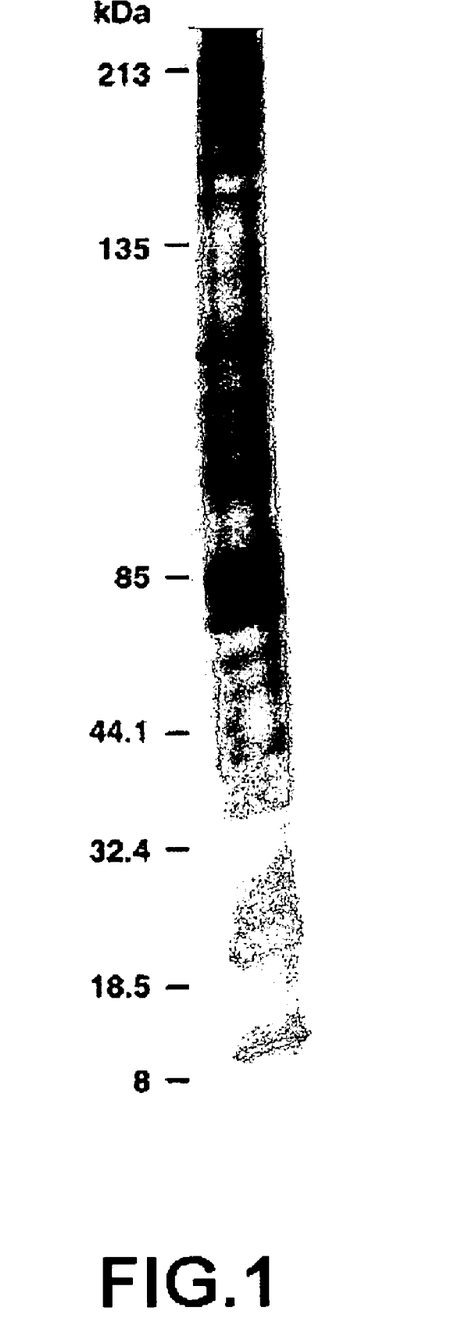
FIGS. 1 to 4 are photographs of electrophorisis gels.

SDS-PAGE profiles (FIG. 1). SDS-PAGE of *T. whippelii* showed more particularly 7 main bands at 10, 20, 80, 120, 150, 170 and 200 kDa.

Production of the Mabs. The supernatant of 4 hybridomas was tested by MIF. Four hybridomas proved specific for *T. whippelii*. One hybridoma was deposited in the CNCM of the Institut Pasteur, 25 rue du Docteur Roux, PARIS 75724, under no. I-2411 and under the identification reference TW 17G2.

Figure 2:
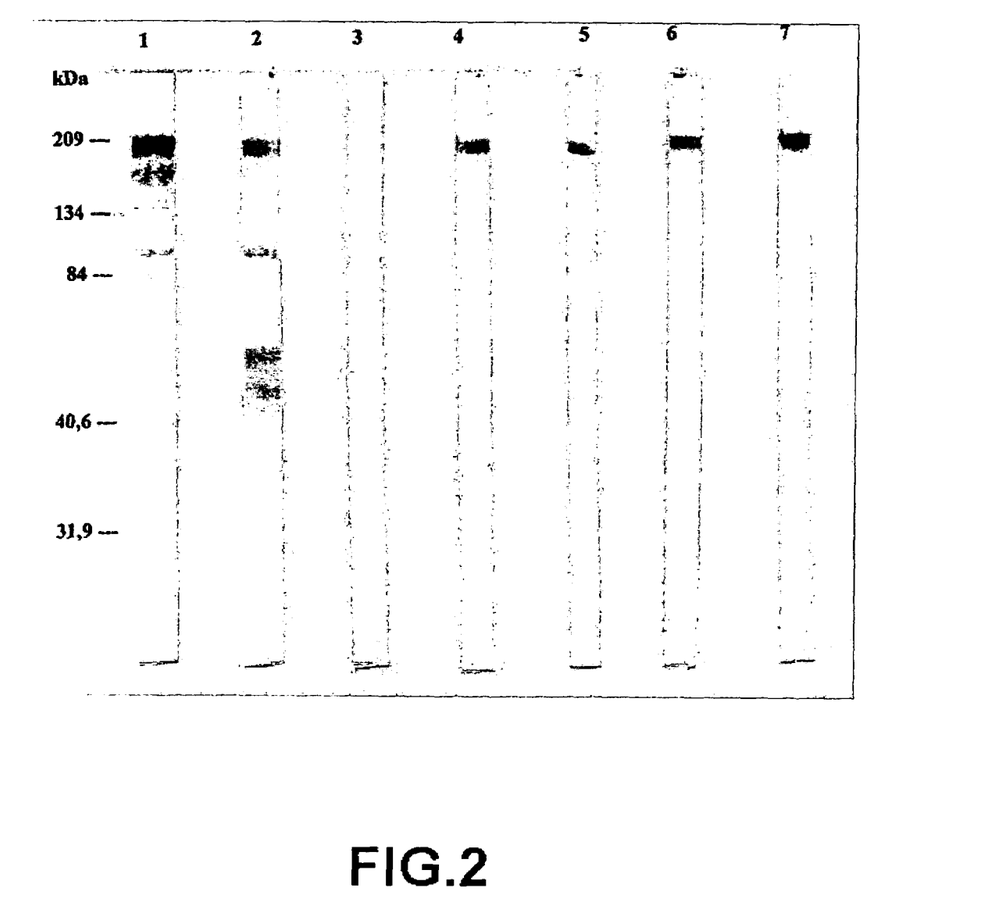
Figure 3:
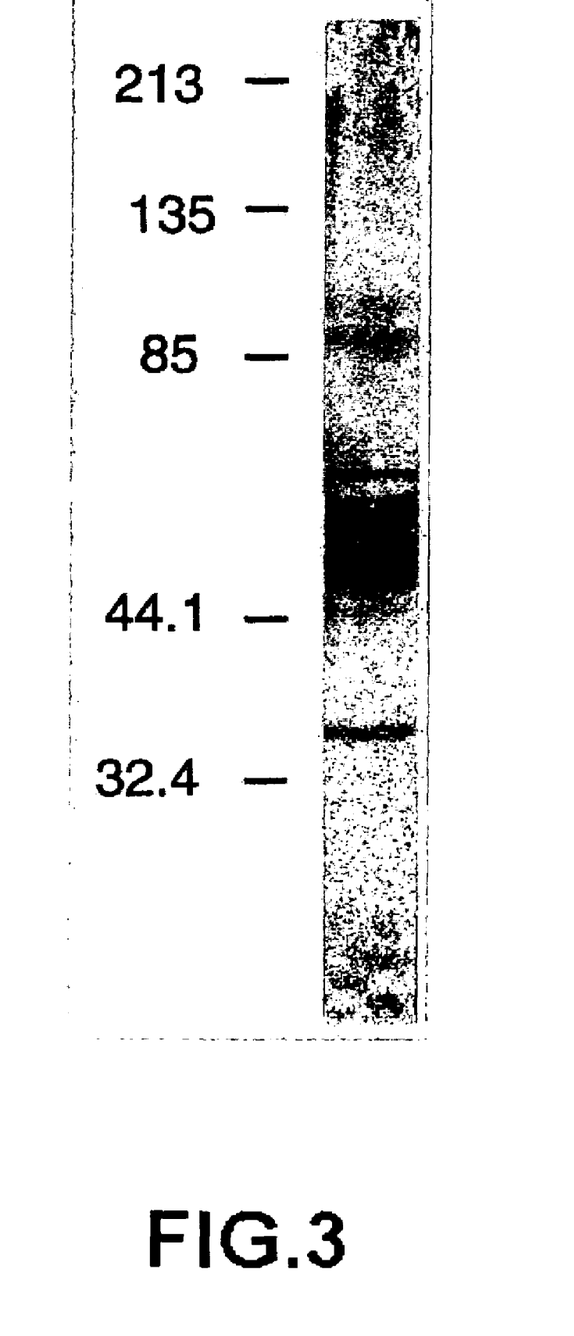

Serological tests performed on the patients. 13 of the 15 patients (86.7%) gave a positive serology test with an IgM level of ≧1:100. The antigen profile observed in Western blotting showed a reactivity with several bands, including a major band at 200 kDa for IgG (FIG. 2). Several protein profiles are identified for IgM, including a reactivity against proteins of 100, 60, 50 and 35 kDa (FIG. 3).

Serological tests performed on the immunized mice and rabbit. The immunized mice and rabbit gave a positive serology test with an IgM level of >1:100. The antigen profile observed in Western blotting showed a different reactivity between mouse and rabbit which differed from that observed in the patients. On the other hand, a major reactivity was observed with a band at 200 kDa.

Characterization of the Mabs (FIG. 2). The 4 Mabs exhibited a specific reactivity for an antigen of 200 kDa, which had already been demonstrated on the Western blots of the patients, mice and rabbit. They were all identified as IgMs. The recognized antigen was destroyed by the action of proteinase K, showing that it was a protein.

Blind tests on the Mabs. The ascites of the 4 hybridomas reacted only with *T. whippelii*.

Example 7

Sequence of the rpoB Gene of *Tropheryma whippelii*

The sequence of the rpoB gene of *Tropheryma whippelii* was determined by enzymatic amplification and direct automatic sequencing using consensus primers.

The sequences of the consensus primers used were as follows:

SEQ ID No 1=5'-TIA TGG GII CIA AIA TGC A-3'
SEQ ID No 2=5'-GCC CAI CAT TCC ATI TCI CC-3' (I=inosine)

DNA extracted from the strain *Tropheryma whippelii* Twist-Marseille CNCM I-2202 by mechanical and chemical lysis (Fast-Prep Bio 101) was incorporated under the following experimental conditions: 35 amplification cycles, each cycle comprising a denaturation of the DNA at 94° C. for 30 sec., an initial hybridization of the primers at 50° C. for 30 sec. including a ramping of −0.1° C. per cycle, and then an elongation at 72° C. for 60 sec.

The sequences SEQ ID No 1 and SEQ ID N° 2 were determined by alignment of the peptide sequences deposited in GenBank under the following accession numbers for the following bacteria: *Bacillus subtilis*, L43593, *Bartonella henselae*, AF171070, *Borrelia burgdorferi*, AE001144, *Buchnera aphidicola*, Z11913, *Chlamydia pneumoniae*, AE001593, *Chlamydia trachomatis*, AE001304, *Coxiella burnetti*, U86688, *Escherichia coli*, U76222, *Haemophilus influenzae*, U32733, *Helicobacter pylori*, E000625, *Legionella pneumophila*, AF087812, *Mycobacterium leprae*, Z14314, *Mycobacterium smegmatis*, U24494, *Mycobacterium tuberculosis*, L27989, *Mycoplasma gallisepticum*, L38402, *Mycoplasma genitalium*, U39715, *Mycoplasma pneumoniae*, AE000030, *Neisseria meningitidis*, Z54353, *Pseudomonas putida*, X15849, *Rickettsia prowazekii*, AF034531, *Rickettsia typhi*, P77941, *Salmonella enterica typhimurium*, X04642, *Spiroplasma citri*, U25815, *Staphylococcus aureus*, U970062, *Synechocystis* spp., D90905, *Thermotoga maritima*, X72695, *Treponema pallidum*, AE001205, and Human Granulocytic Ehrlichiosis agent, AF237414.

The sequences SEQ ID No 1 and 2 were chosen by selecting the sequences which were the most conserved, on the assumption that they were also present in *Tropheryma whippelii*.

The partial sequence of the rpoB gene of Tropheryma whippelii (GenBank accession number AF243072) which corresponds to SEQ ID No 3, obtained with the aid of the primers SEQ ID No 1 and No 2, is as follows:

BASE 157 a 117 c 176 g 150 t 12 others

Example 8

Specific Detection of the rpoB Gene of *Tropheryma whippelii*

The following sequences specific for *Tropheryma whippelii* were selected from the fragment SEQ ID No 3:

SEQ ID No 4: 5'-GCA TTG TGG GGG ATG TTT-3'

SEQ ID No 5: 5'-TTG GGG TCA CCT TAC CAA-3'

They were chosen as being specific for *Tropheryma whippelii* by comparison with the known sequences of the rpoB gene of the 28 above-mentioned bacteria listed in GenBank.

Example 9

Specific Amplification of the rpoB Gene of *Tropheryma whippelii*

Figure 4:
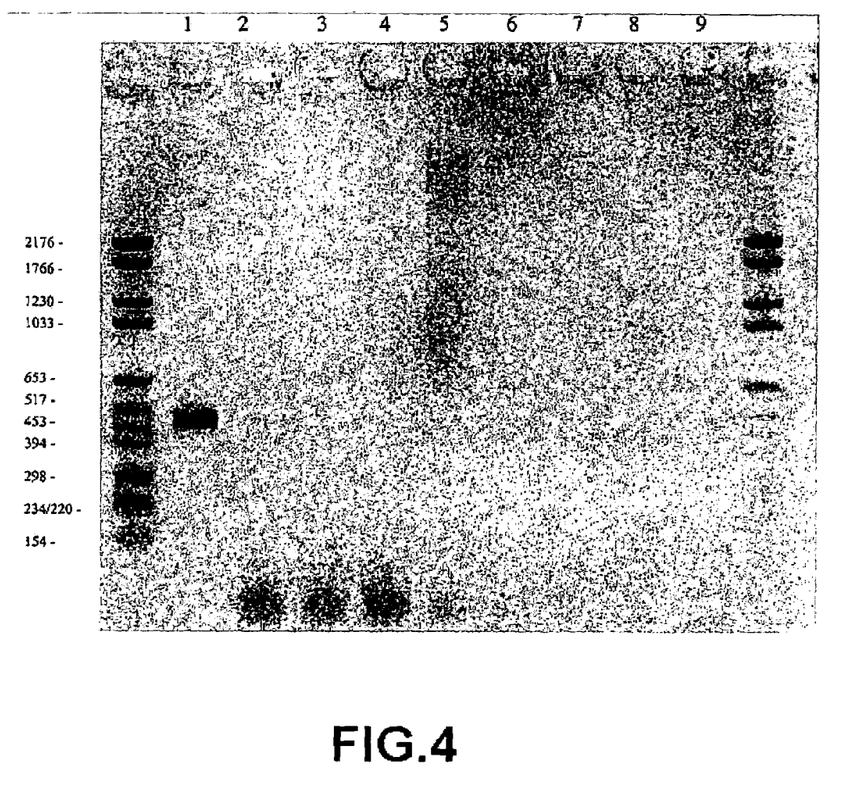

The rpoB gene of *Tropheryma whippelii* was amplified by the PCR technique using 35 amplification cycles each comprising a denaturation phase at 94° C. for 30 seconds, a hybridization phase for the primers SEQ ID No 4 and 5 at 52° C. for 30 seconds and an elongation phase at 72° C. for 90 seconds. The amplification product is visualized after staining with ethidium bromide (FIG. 4).

The control bacteria, namely *Mycobacterium avium*, *Mycobacterium tuberculosis*, *Nocardia otitidiscaviarum*, *Escherichia coli*, *Staphylococcus eperdimilis* and *Corynebacterium amycolatum*, were not detected, demonstrating the specificity of the primers tested.

The rpoB sequences of these control species deposited in GenBank under the following accession numbers: *Mycobacterium avium* ATCC 25291, AF060336, *Mycobacterium tuberculosis*, U12205, and *Escherichia coli* K-12, U77436, were chosen on account of their genetic similarity to *Tropheryma whippelii* or on account of their occurrence as a possible contaminant in the clinical swabs submitted for the detection of *Tropheryma whippelii*.

We claim:

1. A culture comprising a culture medium and a bacterium responsible for Whipple's disease, said bacterium being isolated and established in culture in a cell such that the bacterium can reproducibly and detectably multiply over time in the culture medium for at least 72 days as detected by inverted microscopy, wherein the bacterium is *Tropheryma whippelii.*

2. The culture according to claim 1, wherein said culture is not a cell culture in monocyte cells.

3. The culture according to claim 1, wherein said culture is a cell culture in immortalized cells other than monocyte cells.

4. The culture according to claim 3, wherein the immortalized cells are fibroblast cells.

5. The culture according to claim 1, wherein the cell has a dividing time greater than the doubling time of the bacterium.

6. The culture according to claim 5, wherein the cell is a fibroblast cell.

7. The culture according to claim 1, wherein the bacterium is capable of reproducibly and detectably multiplying over time in said culture medium through successive subcultures.

8. The culture according to claim 1, wherein the bacterium has been established in culture through successive subcultures.

9. The culture according to claim 1, wherein the bacterium is of the *Tropheryma whippelii* bacterium strain deposited in the CNCM of the Institut Pasteur under Deposit No. I-2202.

10. The culture according to claim 1, wherein the bacterium comprises a rpoB gene comprising a partial sequence amplifiable by primers of a sequence identical to SEQ. ID. No.:4 or 5.

11. The culture according to claim 10, wherein said culture medium does not comprise monocyte cells.

12. The culture according to claim 11, wherein the bacterium is of the *Tropheryma whippelii* bacterium strain deposited in the CNCM of the Institut Pasteur under Deposit No. I-2202.

13. The culture according to claim 12, wherein the bacterium is in a cell having a dividing time greater than the doubling time of the bacterium, and the cell is in the culture medium.

14. The culture according to claim 13, wherein the cell is a fibroblast cell.

15. The culture according to claim 1, wherein the bacterium is capable of reproducibly and detectably multiplying over time in a culture medium comprising fibroblast cells.

16. The A culture according to claim 1, wherein the bacterium can reproducibly and detectably multiply over time in the culture medium for 72 days.

17. A culture comprising a culture medium and a bacterium responsible for Whipple's disease, said bacterium being isolated and established in culture in a cell such that the bacterium can reproducibly and detectably multiply over time in the culture medium for at least 72 days through successive subcultures, as detected by inverted microscopy, wherein the bacterium is of the *Tropheryma whippelii* bacterium strain deposited in the CNCM of the Institut Pasteur under Deposit No. I-2202, wherein the bacterium comprises a rpoB gene comprising a partial sequence amplifiable by primers of a sequence identical to SEQ ID NO.:4 or 5.

18. A culture comprising a culture medium and a bacterium responsible for Whipple's disease, said bacterium being isolated and established in culture in a cell in the culture medium, wherein the bacterium is *Tropheryma whippelii,* and said cell has a dividing time greater than the doubling time of the bacterium.

19. A culture comprising a culture medium and a bacterium responsible for Whipple's disease, said bacterium being isolated and established in culture in a cell in the culture medium, wherein the bacterium is *Tropheryma whippelii,* and the cell is selected such that it does not multiply so rapidly relative to the growth of the bacterium as to cause a dilution effect of the bacterium.

20. A process of culturing *Tropheryma whippelii* bacteria responsible for Whipple's disease, comprising isolating and establishing said bacteria in cells in a culture medium such that said bacteria are capable of reproducibly and detectably multiplying over time in the culture medium for at least 72 days as detected by inverted microscopy.

21. The process according to claim 20, wherein said bacteria have a doubling time of 18 days and are in cells having a dividing time greater than 18 days, and the cells are in the culture medium.

22. The process according to claim 20, wherein said bacteria are in cells in the culture medium.

23. The A process according to claim 22, wherein said cells have a dividing time greater than the doubling time of said bacteria.

24. The process according to claim 23, wherein said doubling time is 18 days.

25. The process according to claim 22, wherein said cells are not monocyte cells.

26. The process according to claim 22, wherein said cells are fibroblast cells.

27. The process according to claim 20, wherein the establishing step comprises establishing said bacteria in said culture medium through successive subcultures.

28. The process according to claim 20, wherein the bacteria comprise a rpoB gene comprising a partial sequence amplifiable by primers of a sequence identical to SEQ. ID. No. 4 or 5.

29. The process according to claim 20, wherein the bacteria are of the *Tropheryma whippelii* bacterium strain deposited in the CNCM of the Institut Pasteur under Deposit No. I-2202.

30. The process according to claim 29, wherein said cells in the culture medium have a dividing time greater than the doubling time of said bacteria.

31. The process according to claim 30, comprising establishing said bacteria in said culture medium through successive subcultures.

32. The process according to claim 31, wherein the cells in the culture medium are fibroblast cells.

33. The process according to claim 32, wherein the bacteria are of the *Tropheryma whippelii* bacterium strain deposited in the CNCM of the Institut Pasteur under Deposit No. I-2202.

34. The A process according to claim 20, wherein said culture does not comprise monocyte cells.

35. The process according to claim 20, further comprising maintaining the bacteria in culture for at least 72 days.

36. A process of culturing *Tropheryma whippelii* bacteria responsible for Whipple's disease, comprising isolating and establishing said bacteria in cells in a culture medium such that said bacteria are capable of reproducibly and detectably multiplying over time in the culture medium for at least 72 days through successive subcultures, as detected by inverted microscopy, wherein the bacteria comprise a rpoB gene comprising a partial sequence amplifiable by primers of a sequence identical to SEQ ID NO.:4 or 5, and wherein the bacteria are of the *Tropheryma whippelii* bacterium strain deposited in the CNCM of the Institut Pasteur under Deposit No. I-2202.

37. The process according to claim 36, further comprising maintaining the bacteria in culture for at least 72 days.

38. A method for the in vitro diagnosis of diseases associated with infections caused by *Tropheryma whippelii*, comprising contacting serum or any other biological fluid of a patient with the culture according to claim 1 or a *Tropheryma whippelii* bacterium obtained from said culture, and detecting an immunological reaction.

39. A method for the in vitro diagnosis according to claim 38, comprising:
  depositing a solution containing said *Tropheryma whippelii* bacterium in or on a solid support;
  introducing serum or any other biological fluid into or onto said support;
  introducing a solution of a labeled antibody specific for a human immunoglobulin, which recognizes said bacterium, into or onto the support;
  observing an incubation period;
  rinsing the solid support; and
  detecting an immunological reaction.

40. An antigen isolated from a *Tropheryma whippelii* bacterium in the culture according to claim 1, wherein said antigen is a protein of 200 kD determined by polyacrylamide gel electrophoresis using the Western blotting technique, which reacts with a specific monoclonal antibody directed against the bacterium *Tropheryma whippelii* responsible for Whipple's disease or an antigen of said bacterium, said antibody being produced by a hybridoma deposited in the CNCM of the Institut Pasteur under the Deposit No. 1-2411.

41. A method for the in vitro diagnosis of diseases associated with infections caused by *Tropheryma whippelii*, comprising contacting serum or any other biological fluid of a patient with the antigen of claim 5, and detecting an immunological reaction.

42. The method for the in vitro serological diagnosis according to claim 41, comprising:
  depositing a solution containing said antigen in or on a solid support;
  introducing serum or any other biological fluid into or onto said support;
  introducing a solution of a labeled antibody specific for a human immunoglobulin, which recognizes said antigen, into or onto the support;
  observing an incubation period;
  rinsing the solid support; and
  detecting an immunological reaction.

* * * * *

SEQUENCE LISTING

```
<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(2)
<223> OTHER INFORMATION: n = I
<220> FEATURE:
<221> NAME/KEY: misc_feature
<222> LOCATION: (8)..(8)
<223> OTHER INFORMATION: n = I
<220> FEATURE:
<221> NAME/KEY: misc_feature
<222> LOCATION: (9)..(9)
<223> OTHER INFORMATION: n = I
<220> FEATURE:
<221> NAME/KEY: misc_feature
<222> LOCATION: (11)..(11)
<223> OTHER INFORMATION: n = I
<220> FEATURE:
<221> NAME/KEY: misc_feature
<222> LOCATION: (14)..(14)
<223> OTHER INFORMATION: n = I

<400> SEQUENCE: 1
tnatgggnnc naanatgca                                         19

<210> SEQ ID NO 2
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
```

```
<223> OTHER INFORMATION: n = I
<220> FEATURE:
<221> NAME/KEY: misc_feature
<222> LOCATION: (15)..(15)
<223> OTHER INFORMATION: n = I
<220> FEATURE:
<221> NAME/KEY: misc_feature
<222> LOCATION: (18)..(18)
<223> OTHER INFORMATION: n = I

<400> SEQUENCE: 2
gcccancatt ccatntcncc                                              20

<210> SEQ ID NO 3
<211> LENGTH: 612
<212> TYPE: DNA
<213> ORGANISM: Tropheryma whippelii
<220> FEATURE:
<221> NAME/KEY: misc_feature
<222> LOCATION: (9)..(9)
<223> OTHER INFORMATION: n = a or g or c or t/u, unknown or other
<220> FEATURE:
<221> NAME/KEY: misc_feature
<222> LOCATION: (16)..(16)
<223> OTHER INFORMATION: n = a or g or c or t/u, unknown or other
<220> FEATURE:
<221> NAME/KEY: misc_feature
<222> LOCATION: (18)..(18)
<223> OTHER INFORMATION: n = a or g or c or t/u, unknown or other
<220> FEATURE:
<221> NAME/KEY: misc_feature
<222> LOCATION: (22)..(22)
<223> OTHER INFORMATION: n = a or g or c or t/u, unknown or other
<220> FEATURE:
<221> NAME/KEY: misc_feature
<222> LOCATION: (29)..(29)
<223> OTHER INFORMATION: n = a or g or c or t/u, unknown or other
<220> FEATURE:
<221> NAME/KEY: misc_feature
<222> LOCATION: (38)..(38)
<223> OTHER INFORMATION: n = a or g or c or t/u, unknown or other
<220> FEATURE:
<221> NAME/KEY: misc_feature
<222> LOCATION: (68)..(68)
<223> OTHER INFORMATION: n = a or g or c or t/u, unknown or other
<220> FEATURE:
<221> NAME/KEY: misc_feature
<222> LOCATION: (117)..(118)
<223> OTHER INFORMATION: n = a or g or c or t/u, unknown or other
<220> FEATURE:
<221> NAME/KEY: misc_feature
<222> LOCATION: (195)..(195)
<223> OTHER INFORMATION: n = a or g or c or t/u, unknown or other
<220> FEATURE:
<221> NAME/KEY: misc_feature
<222> LOCATION: (379)..(379)
<223> OTHER INFORMATION: n = a or g or c or t/u, unknown or other
<220> FEATURE:
<221> NAME/KEY: misc_feature
<222> LOCATION: (436)..(436)
<223> OTHER INFORMATION: n = a or g or c or t/u, unknown or other

<400> SEQUENCE: 3
aagtccccng acggnanag gnatggagng gtatgtancg atcgatgcgg gtgatgtttt    60
aattgccnag gatccgggca ttgtggggga tgtttccgct gatgttgtca ctgtcannca  120
ggatgacggg aaacatcgcg actaccatgt tggtaaattt gttcgttcaa atcagggcaa  180
ctgttacaac cagcnagttg tggtccgatc cggagatcgt gtataaaaag gtacagttct  240
tgcacatggt ccatgtactg acaaaggtga gcttagtctt ggtagaaatc ttctggttgc  300
tttcatgccc tgggagggct ataactttga ggatgcgata attatcagcc agaatttggt  360
caaggacgac acccctttcnt caatccacat agaagaacat gaggttagca cccgggatac  420
```

```
                                         -continued gaagctgggc agtganagaa ataacgcgag accttccgaa tgtaagcatg gattacataa      480
aggacttgga cgaacggggt attatccgga ttggcgctga ggttggccct ggggacattt      540
tggttggtaa ggtgacccca aagggcgaag accgaactca acgcggaaga acgtttgctg      600
agggctatct tt                                                         612

<210> SEQ ID NO 4
<211> LENGTH: 18
<212> TYPE: DNA
<213> ORGANISM: Artificial Sequence
<220> FEATURE:
<223> OTHER INFORMATION: oligonucleotide

<400> SEQUENCE: 4
gcattgtggg ggatgttt                                                    18

<210> SEQ ID NO 5
<211> LENGTH: 18
<212> TYPE: DNA
<213> ORGANISM: Artificial Sequence
<220> FEATURE:
<223> OTHER INFORMATION: oligonucleotide

<400> SEQUENCE: 5
ttggggtcac cttaccaa                                                    18
```